United States Patent [19]

Mais et al.

[11] Patent Number: 4,827,058

[45] Date of Patent: May 2, 1989

[54] PROCESS FOR THE REMOVAL OF M-CHLOROTOLUENE FROM CHLOROTOLUENE MIXTURES

[75] Inventors: Franz-Josef Mais, Duesseldorf; Helmut Fiege, Leverkusen, both of Fed. Rep. of Germany

[73] Assignee: Bayer Aktiengesellschaft, Leverkusen, Fed. Rep. of Germany

[21] Appl. No.: 166,590

[22] Filed: Mar. 10, 1988

[30] Foreign Application Priority Data

Mar. 21, 1987 [DE] Fed. Rep. of Germany ....... 3709415

[51] Int. Cl.$^4$ .................. C07C 17/38; C07C 21/24
[52] U.S. Cl. .................................. 570/211; 570/206; 570/207; 570/208; 570/210
[58] Field of Search ............... 570/207, 210, 211, 206, 570/208

[56] References Cited

U.S. PATENT DOCUMENTS 3,655,783  4/1972  Bacha .................... 570/211
4,748,287  5/1988  Röhlk et al. ............ 570/211

Primary Examiner—Werren B. Lone
Attorney, Agent, or Firm—Sprung Horn Kramer & Woods

[57] ABSTRACT m-Chlorotoluene is removed from chlorotoluene mixtures with a content of up to 10% by weight of m-chlorotoluene, with reference to the total amount of chlorotoluene in the mixture, by chlorinating a substantially toluene-free chlorotoluene mixture in the presence of a Friedel-Crafts catalyst and if appropriate a co-catalyst at from 0° C. up to the boiling point of the mixture, until the content of m-chlorotoluene has decreased to a value of <1.0% by weight in the chlorotoluene mixture.

20 Claims, No Drawings

PROCESS FOR THE REMOVAL OF M-CHLOROTOLUENE FROM CHLOROTOLUENE MIXTURES

BACKGROUND OF THE INVENTION

The invention relates to a process for the removal of m-chlorotoluene from chlorotoluene mixtures with a content of up to 10% by weight of m-chlorotoluene, with reference to the total amount of chlorotoluene in the mixture.

Chlorotoluenes in isomerically pure form are valuable intermediates for pharmaceuticals and agricultural chemicals (Ullmans Enzyklopädie der technischen Chemie, [Ullmann's Encylopaedia of industrial chemistry], 4th edition, volume 9, page 514). The requirement on the purity of the chlorotoluenes is high, particularly in the area of active substances.

A process for the extraction of m-chlorotoluene has been disclosed in U.S. Pat. No. 3,655,783, in which m-chlorotoluene is extracted from a mixture of dichlorotoluenes by addition of HF/BF$_3$ and an organic solvent. The disadvantages connected with the addition of the fluorine compounds, such as the employment of expensive materials for the prevention of damage by corrosion and high expenditure on apparatus for safe handling of the HF/BF$_3$ mixture, are obvious. The addition of a solvent, which considerably complicates later working up by distillation, is also disadvantageous.

A process for the separation of mixed monochlorotoluenes by adsorption on a column filled with zeolite and subsequent desorption with readsorbants has been disclosed in EP-PS (European Patent Specification) No. 0,099,161. However, in this process the very high technical complexity with which the separation is realized is disadvantageous. Additional solvents, such as toluene or chlorobenzene, are required, so that additional distillations are necessary for working up the mixture.

Furthermore, separation of a mixture of the three chlorotoluene isomers by initial fractionation and removal of the m-chlorotoluene remaining in the p-chloro-toluene by multistage crystallization of the melt is known (Ullmans Enzyklopädie technischen Chemie [Ullman's Encyclopaedie of industrial chemistry], 4th edition, volume 9, page 513.) The high technical complexity and the considerable losses of p-chlorotoluene, which in contrast to o-chlorotoluene is a substantially more valuable chlorotoluene isomer, are disadvantageous.

SUMMARY OF THE INVENTION

A process for the removal of m-chlorotoluene from chlorotoluene mixtures with a content of up to 10% by weight of m-chlorotoluene, with reference to the total amount of chlorotoluenes in the mixture, has now been found, which is characterized in that a substantially toluene-free chlorotoluene mixture is chlorinated in the presence of a Friedel-Crafts catalyst and if appropriate a co-catalyst at from 0° C. to the boiling point of the mixture, until the content of m-chlorotoluene has decreased to a value of <1.0% by weight in the chlorotoluene mixture.

DETAILED DESCRIPTION OF THE INVENTION

According to the process according to the invention, the content of toluene in the chlorotoluene mixture should be <2% by weight, preferably <1% by weight, very particularly preferably <0.5% by weight.

In the process according to the invention, chlorotoluene mixtures are employed which have a content of m-chlorotoluene of up to 10% by weight, with reference to the total amount of chlorotoluenes in the mixture. Chlorotoluene mixtures which have a content of up to 2.5% by weight of m-chlorotoluene, with reference to the total amount of chlorotoluenes in the mixture, are particularly preferably employed in the process according to the invention. For example, chlorotoluene mixtures as are obtained from the ring chlorination of toluene, for example in the liquid phase in the presence of catalysts (compare Ullmans Enzyklopädie der technischen Chemie [Ullmann's Encyclopaedia of industrial chemistry], 4th edition, volume 9, page 510) can be employed in the process according to the invention. Depending on the manner of preparation, such chlorotoluene mixtures consists of about 0.3 to 5% by weight of m-chlorotoluene and about 70 to 98% by weight of a mixture of o- and p-chlorotoluene, where the o/p-ratio varies in the range 3:1 to 0.8:1 (o-:p-chlorotoluene). The remainder consists of unreacted toluene as well as di- and if appropriate trichlorotoluenes.

The remaining toluene is removed from the product mixture obtained in the ring chlorination by distillation in the customary manner. A practically toluene-free bottom product remains behind, which, depending on the manner of preparation, consists of 0.5 to 10% by weight of m-chlorotoluene, up to 98% by weight of a mixture of o- and p-chlorotoluene and a residue of more highly chlorinated chlorotoluenes.

In addition to the chlorotoluene mixtures described above, it is also possible according to the process according to the invention to employ any mixtures from another source with up to 10% by weight of m-chlorotoluene, with reference to the total amount of chlorotoluenes in the mixture.

The following compounds can be employed as Friedel-Crafts catalysts in the process according to the invention: manganese chlorides, molybdenum chlorides, titanium chlorides, iron(III) chloride, aluminium chloride, zinc chloride, tin chlorides, antimony chlorides or mixtures of the above compounds, iron(III) chloride, aluminium chloride, antimony(III) chloride, antimony(V) chloride and/or zinc chloride being preferable and iron(III) chloride very particularly preferable. The amount of Friedel-Crafts catalyst to be employed is not critical and is customarily up to 5% by weight, preferably 0.001 to 1% by weight, with reference to the amount of chlorotoluene.

Furthermore, co-catalysts can be added to these Friedel-Crafts catalysts. Those which may be mentioned are: sulphur and/or sulphur compounds, for example diphenyl sulphide, disulphur dichloride, thianthrene, thianthrene derivatives, phenoxathiin, phenoxathiin derivatives, phenothiazine and phenothiazine derivatives, as well as iodine and/or iodine compounds. The co-catalysts sulphur, S$_2$Cl$_2$ and/or iodine are preferred. The amount of co-catalysts is customarily 0.001 to 5% by weight, preferably 0.01 to 1% by weight, with reference to the total amount of chlorotoluene in the mixture.

The employment of a Friedel-Crafts catalyst with a co-catalyst is preferred according to the invention. The use of co-catalysts is particularly favourable for the process according to the invention, since the formation of higher chlorotoluenes is then reduced. The further chlorination of p-chlorotoluene, a substantially more valuable chlorotoluene isomer than o-chlorotoluene, is, in particular, reduced in comparison with the chlorination without co-catalysts.

The ratio of amounts of Friedel-Crafts catalyst to co-catalyst is generally 10:1 to 1:10, preferably 2:1 to 1:2.

The chlorination of the chlorotoluene mixture is carried out at temperatures from about 0° C. up to the boiling point of the mixture, preferably 20° to 80° C., particularly preferably 30° to 50° C.

The chlorination according to the invention can be carried out at atmospheric pressure, reduced pressure or elevated pressure. Atmospheric pressure is preferred.

According to the invention, the chlorination can be carried out using elemental chlorine in gaseous or in liquid form. It is also possible to use equivalent amounts of other chlorinating agents, that is chlorine-containing compounds which can give off in a reactive form under the selected reaction conditions the chlorine contained. For example, such chlorinating agents which may be mentioned are: sulphuryl chloride, chlorine oxides, such as chlorine monoxide, chlorosulphonic acid and/or thionyl chloride. According to the invention, gaseous chlorine is preferably employed.

According to the process according to the invention, the chlorination of the chlorotoluene mixture is continued until the content of m-chlorotoluene has decreased to a value of <1.0% by weight, preferably <0.5% by weight, particularly preferably <0.1% by weight, very particularly preferably 0.05% by weight in the chlorotoluene mixture. Of course, it is also possible according to the process according to the invention to control the chlorination until a higher or lower content of m-chlorotolune than the abovementioned has established itself in the chlorotoluene mixture. According to the process according to the invention, it is extremely simple to determine the progress of the decrease of the amount of m-chlorotoluene, for example by gas chromatographic analysis, and to discontinue the introduction of the chlorinating agent when the desired low content of m-chlorotoluene in the chlorotoluene mixture is achieved.

The process according to the invention can be carried out both continuously and discontinuously.

After completion of the chlorination according to the invention, the o/p-chlorotoluene mixture can be worked up in a customary manner. o- and p-chlorotoluene isomers of extremely high purity are obtained by distillation.

In a particularly preferred embodiment of the process according to the invention, no additional Friedel-Crafts catalyst or co-catalyst is added to the chlorotoluene mixture which is obtained from the ring chlorination of toluene and which after removal of the residual toluene by distillation still contains the catalyst or the catalyst mixture added in the ring chlorination and if appropriate at least one co-catalyst. The catalysts already contained in the chlorotoluene mixture and if appropriate the co-catalysts contained therein then serve for the catalysis of the chlorination. The type of the catalyst and if appropriate co-catalyst contained in the chlorotoluene mixture is not critical for carrying out the process according to the invention, that is, a Friedel-Crafts catalyst and if appropriate a co-catalyst suitable for the ring chlorination of toluene according to the prior art is also suitable for the present process according to the invention.

It is surprising that in the process according to the invention practically only the m-chlorotoluene is chlorinated up to higher chlorotoluenes and that the o- and p-chlorotoluene is not substantially further chlorinated under these conditions, in which, especially, hardly any losses occur of the, in comparison with o-chlorotoluene, more valuable p-chlorotoluene. If the process according to the invention is carried out in the presence of at least one co-catalyst, then the losses of p-chlorotoluene are lower still. Furthermore, it is surprising that the m-chlorotoluene content in the chlorotoluene mixture practially disappears even on very slight overchlorination.

The process according to the invention is industrially particularly advantageous, since it facilitates removal of the m-chlorotoluene at low cost in simple apparatussus. It is very particularly advantageous that the process according to the invention can be applied to crude chlorotoluene mixtures such as result from the ring chlorination of toluene. Previous purification of the chlorotoluene mixture is therefore no longer necessary. The separation of the chlorotoluene isomers can be performed without great cost after carrying out the process according to the invention.

The following examples serve to illustrate the process according to the invention, but without limiting it to these examples.

Example 1

100 parts by weight of the chlorotoluene mixture were placed in a reactor fitted with a stirrer as well as a gas inlet and outlet. The stated parts by weight of catalyst and co-catalyst were added and gaseous chlorine was introduced. As soon as a desired low content of m-chlorotoluene had been established by gas chromatographic monitoring, the introduction of chlorine was discontinued.

Mixture employed 51.55% of o-chlorotoluene (o-ClT)
0.40% of m-chlorotoluene (m-ClT)
47.94% of p-chlorotoluene (p-ClT)
0.11% of dichlorotoluenes (diClT)
0.025% by weight of $FeCl_3$
0.015% by weight of $S_2Cl_2$

| Temp. | $Cl_2$/mol % | o-ClT | m-ClT | p-ClT | diClT |
| --- | --- | --- | --- | --- | --- |
| 27° C. | 1.06 | 51.23 | 0.28 | 47.77 | 0.72 |
| 31° C. | 3.33 | 50.39 | 0.12 | 47.39 | 2.10 |
| 32° C. | 6.70 | 49.09 | 0.02 | 46.90 | 3.99 |

The Examples 2–6 below were carried out according to the directions of Example 1. In the examples, the composition of the chlorotoluene mixture employed and the amount and type of catalyst and co-catalyst are given in each case.

Example 2

Mixture employed 48.66% of o-chlorotoluene
1.74% of m-chlorotoluene
49.57% of p-chlorotoluene
0.03% of dichlorotoluenes
0.015% by weight of $FeCl_3$
0.015% by weight of $S_2Cl_2$

| Temp. | Cl$_2$/mol % | o-ClT | m-ClT | p-ClT | diClT |
|---|---|---|---|---|---|
| 30° C. | 3.33 | 47.81 | 0.69 | 48.99 | 2.54 |
| 32° C. | 6.62 | 46.21 | 0.19 | 48.34 | 5.26 |
| 33° C. | 11.75 | 44.29 | 0.02 | 47.19 | 8.50 |

Example 3

Mixture employed 49.12% of o-chlorotoluene
0.93% of m-chlorotoluene
49.87% of p-chlorotoluene
0.04% of dichlorotoluenes
0.015% by weight of FeCl$_3$
0.015% by weight of S$_2$Cl$_2$

| Temp. | Cl$_2$/mol % | o-ClT | m-ClT | p-ClT | DiClT |
|---|---|---|---|---|---|
| 30° C. | 3.45 | 47.97 | 0.28 | 49.16 | 2.59 |
| 32° C. | 6.90 | 46.61 | 0.08 | 48.55 | 4.76 |
| 33° C. | 10.11 | 45.15 | 0.01 | 47.80 | 7.04 |

Example 4

Mixture employed 49.34% of o-chlorotoluene
0.50% of m-chlorotoluene
50.10% of p-chlorotoluene
0.06% of dichlorotoluenes
0.015% by weight of FeCl$_3$
0.015% by weight of S$_2$Cl$_2$

| Temp. | Cl$_2$/mol % | o-ClT | m-ClT | p-ClT | diClT |
|---|---|---|---|---|---|
| 32° C. | 3.41 | 47.22 | 0.11 | 49.26 | 3.41 |
| 33° C. | 6.75 | 46.13 | 0.02 | 48.50 | 5.35 |

Example 5

Mixture employed 0.21% of o-chlorotoluene
0.72% of m-chlorotoluene
99.07% of p-chlorotoluene
0.030% by weight of FeCl$_3$
0.015% by weight of sulphur

| Temp. | Cl$_2$/mol % | Tol. | o-ClT | m-ClT | p-ClT | DiClT |
|---|---|---|---|---|---|---|
| 30° C. | 3.39 | — | 0.21 | 0.20 | 97.23 | 2.36 |
| 32° C. | 6.77 | — | 0.20 | 0.03 | 95.04 | 4.73 |

Example 6

Mixture employed 76.16% of o-chlorotoluene
0.64% of m-chlorotoluene
20.18% of p-chlorotoluene
0.02% of dichlorotoluenes
0.030% by weight of SbCl$_3$
0.015% by weight of S$_2$Cl$_2$

| Temp. | Cl$_2$/mol % | o-ClT | m-ClT | p-ClT | diClT |
|---|---|---|---|---|---|
| 40° C. | 6.58 | 75.55 | 0.03 | 19.68 | 4.74 |

Example 7

100 parts by weight of the chlorotoluene mixture were placed in a reactor fitted with a stirrer and a gas inlet and outlet. The stated amount of catalyst was added and gaseous chlorine was introduced until the desired content of m-chlorotoluene had been established according to GC analysis.

Mixture employed 49.43% of o-chlorotoluene
0.47% of m-chlorotoluene
50.10% of p-chlorotoluene
0.025% by weight of FeCl$_3$

| Temp. | Cl$_2$/mol % | o-ClT | m-ClT | p-ClT | diClT |
|---|---|---|---|---|---|
| 27° C. | 4.59 | 49.05 | 0.35 | 49.79 | 0.81 |
| 30° C. | 9.22 | 47.41 | 0.13 | 48.54 | 3.92 |
| 31.5° C. | 11.51 | 46.28 | 0.03 | 47.84 | 5.85 |

Example 8

100 parts by weight of toluene were placed in a reactor with stirring and the stated amounts of catalyst and co-catalyst were added. After this, as customary in accordance with the prior art, the toluene was chlorinated to give a mixture of toluene, isomeric chlorotoluenes and higher chlorotoluenes. After, the residual toluene had been removed by an industrially conventional distillation, gaseous chlorine was introduced into the mixture of the given composition at the given temperature until the desired content of m-chlorotoluene had been established by GC analysis.

Mixture employed 0.10% of toluene
51.05% of o-chlorotoluene
0.27% of m-chlorotoluene
46.58% of p-chlorotoluene
2.00% of dichlorotoluenes
Residual catalyst of ring chlorination
ca. 0.01% by weight of FeCl$_3$
ca. 0.01% by weight of sulphur

| Temp. | Cl$_2$/mol % | Toluene | o-ClT | m-ClT | p-ClT | diClT |
|---|---|---|---|---|---|---|
| 36° C. | 3.18 | 0.03 | 50.37 | 0.12 | 46.31 | 3.17 |
| 36° C. | 5.54 | 0.01 | 48.50 | 0.01 | 45.76 | 5.72 |

Example 9 was carried out as Example 8, only another catalyst and another co-catalyst were used in accordance with the prior art.

Example 9

Mixture employed 0.14% of toluene
45.48% of o-chlorotoluene
0.43% of m-chlorotoluene
53.49% of p-chlorotoluene
0.36% of dichlorotoluenes
Residual catalyst from the ring chlorination 0.100% by weight of 2,7-dichlorothianthrene
0.027% by weight of SbCl₃

| Temp. | Cl₂/mol % | Toluene | o-ClT | m-ClT | p-ClT | diClT |
|---|---|---|---|---|---|---|
| 50° C. | 3.39 | 0.02 | 44.73 | 0.19 | 53.21 | 1.87 |
| 50° C. | 8.63 | — | 42.19 | 0.02 | 52.14 | 5.65 |

Example 10

100 parts by weight of the chlorotoluene mixture were placed in a reactor fitted with a stirrer and gas outlet. The stated parts by weight of catalyst and co-catalyst were added and 13 mol % of liquid sulphuryl chloride were introduced. The reaction mixture were stirred for 12 hours at the given temperature and washed with the equivalent volume of water.

Mixture employed 49.40% of o-chlorotoluene
0.46% of m-chlorotoluene
50.14% of p-chlorotoluene
0.07% by weight of FeCl₃
0.07% by weight of sulphur

| Temp. | o-ClT | m-ClT | p-ClT | diClT |
|---|---|---|---|---|
| 40° C. | 46.03 | 0.02 | 48.82 | 5.13 |

What is claimed is:

1. A process for the removal of m-chlorotoluene from chlorotoluene mixtures having a content of up to 10% by weight of-chlorotoluene, with reference to the total amount of chlorotoluenes in the mixture, characterized in that a sustantially toluene-free chlorotoluene mixture is chlorinated in the presence of a Friedel-Crafts catalyst at from 0° C. up to the boiling point of the mixture, until the content of m-chlorotoluene has decreased to a value of <1.0% by weight in the chlorotoluene mixture.

2. A process according to claim 1, characterized in that it is carried out in the presence of a co-catalyst.

3. A process according to claim 1, characterized in that the toluene content in the chlorotoluene mixture is less than 2% by weight.

4. A process according to claim 3, characterized in that the toluene content in the chlorotoluene mixture is less than 1% by weight.

5. A process according to claim 4, characterized in that the toluene content in the chlorotoluene mixture is less than 0.5% by weight.

6. A process according to claim 1, characterized in that iron (III) chloride, aluminium chloride, antimony(III) chloride, antimony(V)chloride and/or zinc chloride are employed as Friedel-Crafts catalysts.

7. A process according to claim 2, characterized in that sulphur, sulphur compounds, iodine and/or iodine compounds are employed as co-catalysts.

8. A process according to claim 7, characterized in that disulphur dichloride, diphenyl sulphide, thianthrene, thianthrene derivatives, phenoxathiin, phenoxathiin derivatives, phenothiazine or phenothiazine derivatives are employed as sulphur compounds.

9. A process according to claim 1, characterized in that the chlorination is carried out with gaseous or liquid chlorine or an equivalent amount of another chlorinating agent.

10. A process according to claim 9, characterized in that sulphuryl chloride is used as chlorinating agent.

11. A process according to claim 1, characterized in that a crude, substantially toluene-free chlorotoluene mixture from the chlorotoluene preparation is employed which still contains the Friedel-Crafts catalyst.

12. A process according to claim 11, characterized in that a crude, substantially toluene-free chlorotoluene mixture from the chlorotoluene preparation is employed which in addition still contains a co-catalyst.

13. A process according to claim 1, characterized in that the chlorination is carried out at a temperature of 20° to 80° C.

14. A process according to claim 1, characterized in that 0.001-5% by weight of the Friedel-Crafts catalyst is employed.

15. A process according to claim 14, characterized in that 0.001-1% by weight of the Friedel-Crafts catalyst is employed.

16. A process according to claim 7, characterized in that 0.001-5% by weight of the co-catalyst is employed.

17. A process according to claim 16, characterized in that 0.01-1% by weight of the co-catalyst is employed.

18. A process according to claim 1, characterized in that the ratio of amounts of the Friedel-Crafts catalyst to the co-catalyst is 10:1 to 1:10.

19. A process according to claim 18, characterized in that the ratio of amounts of the Friedel-Crafts catalyst to co-catalyst is 2:1 to 1:2.

20. A process according to claim 13, characterized in that the chlorination is carried out at a temperature of 30° to 50° C.

* * * * *